United States Patent
Ambeck-Madsen et al.

(10) Patent No.: US 12,094,213 B2
(45) Date of Patent: Sep. 17, 2024

(54) CONTROL DEVICE, SYSTEM AND METHOD FOR DETERMINING PERCEPTUAL LOAD OF A VISUAL AND DYNAMIC DRIVING SCENE IN REAL TIME

(71) Applicants: TOYOTA MOTOR EUROPE, Brussels (BE); MINDVISIONLABS LIMITED, London (GB)

(72) Inventors: Jonas Ambeck-Madsen, Brussels (BE); Gabriel Othmezouri, Brussels (BE); Daniel Olmeda Reino, Brussels (BE); Nilli Lavie, London (GB); Luke Palmer, London (GB); Petar Palasek, London (GB)

(73) Assignees: TOYOTA MOTOR EUROPE, Brussels (BE); MINDVISIONLABS LIMITED, London (GB)

( * ) Notice: Subject to any disclaimer, the term of this patent is extended or adjusted under 35 U.S.C. 154(b) by 449 days.

(21) Appl. No.: 17/620,441

(22) PCT Filed: Jun. 20, 2019

(86) PCT No.: PCT/EP2019/066404
§ 371 (c)(1),
(2) Date: Dec. 17, 2021

(87) PCT Pub. No.: WO2020/253965
PCT Pub. Date: Dec. 24, 2020

(65) Prior Publication Data
US 2022/0327840 A1    Oct. 13, 2022

(51) Int. Cl.
| | |
|---|---|
| *G06V 20/56* | (2022.01) |
| *A61B 5/00* | (2006.01) |
| *B60W 40/04* | (2006.01) |
| *B60W 40/08* | (2012.01) |
| *B60W 50/00* | (2006.01) |
| *B60W 60/00* | (2020.01) |
| *G06T 7/11* | (2017.01) |

(Continued)

(52) U.S. Cl.
CPC ............ *G06V 20/56* (2022.01); *A61B 5/0075* (2013.01); *A61B 5/0082* (2013.01); *B60W 40/04* (2013.01);

(Continued)

(58) Field of Classification Search
None
See application file for complete search history.

(56) References Cited

U.S. PATENT DOCUMENTS

| | | | |
|---|---|---|---|
| 2004/0088095 A1 | 5/2004 | Eberle et al. | |
| 2010/0241021 A1* | 9/2010 | Morikawa | G08B 21/06 600/544 |
| 2021/0357670 A1* | 11/2021 | Wu | G06V 20/56 |

OTHER PUBLICATIONS

J. Kim and J. Canny, "Interpretable learning for self-driving cars by visualizing causal attention," 2017 IEEE International Conference on Computer Vision (ICCV), Oct. 2017. doi: 10.1109/iccv.2017.320 (Year: 2017).*

(Continued)

*Primary Examiner* — Vu Le
*Assistant Examiner* — Charles C L Penny
(74) *Attorney, Agent, or Firm* — Oliff PLC

(57) ABSTRACT

A control device for a vehicle for determining perceptual load of a visual and dynamic driving scene, the control device being configured to: receive an image sequence representing the driving scene, extract a set of scene features from the image sequence, the set of scene features representing static and/or dynamic information of the driving scene, calculate a time-aggregated representation of the image sequence based on the extracted set of scene features, calculate an attention map of the driving scene by attentional pooling of the time-aggregated representation of the image sequence, and determine the perceptual load of the driving scene based on the attention map. The invention further relates to a corresponding method.

23 Claims, 3 Drawing Sheets

(51) Int. Cl.
  *G06V 10/44*   (2022.01)
  *G06V 10/62*   (2022.01)
  *G06V 10/762*  (2022.01)
  *G06V 10/77*   (2022.01)
  *G06V 10/774*  (2022.01)
  *G06V 10/82*   (2022.01)

(52) U.S. Cl.
  CPC ........ *B60W 40/08* (2013.01); *B60W 50/0097* (2013.01); *G06T 7/11* (2017.01); *G06V 10/454* (2022.01); *G06V 10/62* (2022.01); *G06V 10/762* (2022.01); *G06V 10/7715* (2022.01); *G06V 10/774* (2022.01); *G06V 10/82* (2022.01); *B60W 60/001* (2020.02); *B60W 2420/40* (2013.01); *B60W 2420/403* (2013.01); *G06T 2207/10016* (2013.01); *G06T 2207/10048* (2013.01); *G06T 2207/20076* (2013.01); *G06T 2207/30252* (2013.01)

(56) References Cited

OTHER PUBLICATIONS

Rohit Girdhar and Deva Ramanan. Attentional pooling for action recognition. In Advances in Neural Information Processing Systems, pp. 34-45, 2017 (Year: 2017).*

L. Palmer, A. Bialkowski, G. J. Brostow, J. Ambeck-Madsen and N. Lavie, "Predicting the Perceptual Demands of Urban Driving with Video Regression," 2017 IEEE Winter Conference on Applications of Computer Vision (WACV), Santa Rosa, CA, USA, 2017, pp. 409-417, doi: 10.1109/WACV.2017.52 (Year: 2017).*

A. Tawari, P. Mallela and S. Martin, "Learning to Attend to Salient Targets in Driving Videos Using Fully Convolutional RNN," 2018 21st International Conference on Intelligent Transportation Systems (ITSC), Maui, HI, USA, 2018, pp. 3225-3232, doi: 10.1109/ITSC.2018.8569438 (Year: 2018).*

W. Wang, J. Shen, F. Guo, M.-M. Cheng and A. Borji, "Revisiting Video Saliency: A Large-Scale Benchmark and a New Model," 2018 IEEE/CVF Conference on Computer Vision and Pattern Recognition, Salt Lake City, UT, USA, 2018, pp. 4894-4903, doi: 10.1109/CVPR.2018.00514 (Year: 2018).*

J. Zheng, T.-Y. Lee, C. Feng, X. Lit and Z. Zhang, "Robust Attentional Pooling via Feature Selection," 2018 24th International Conference on Pattern Recognition (ICPR), Beijing, China, 2018, pp. 2038-2043, doi: 10.1109/ICPR.2018.8545607 (Year: 2018).*

Mar. 19, 2020 Written Opinion issued in International Patent Application No. PCT/EP2019/066404.

Mar. 19, 2020 International Search Report issued in International Patent Application No. PCT/EP2019/066404.

Tamatsu et al.; "Application of Image Recognition Technology to Vehicles"; Encyclopedia of Automotive Engineering. Online; 2014; DOI: 10.1002/9781118354179.auto224.

Jiang et al.; "Deep VS: A Deep Learning Based Video Saliency Prediction Approach"; ECCV; 2018; pp. 625-642.

* cited by examiner

[Fig. 1]
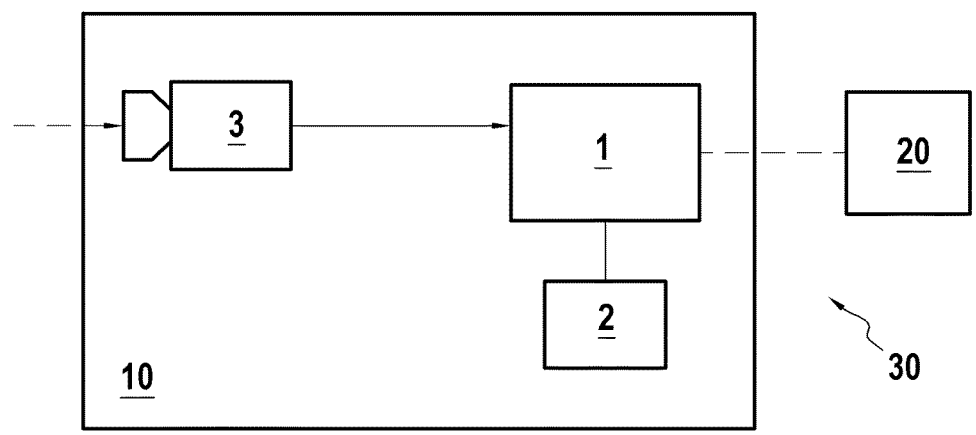

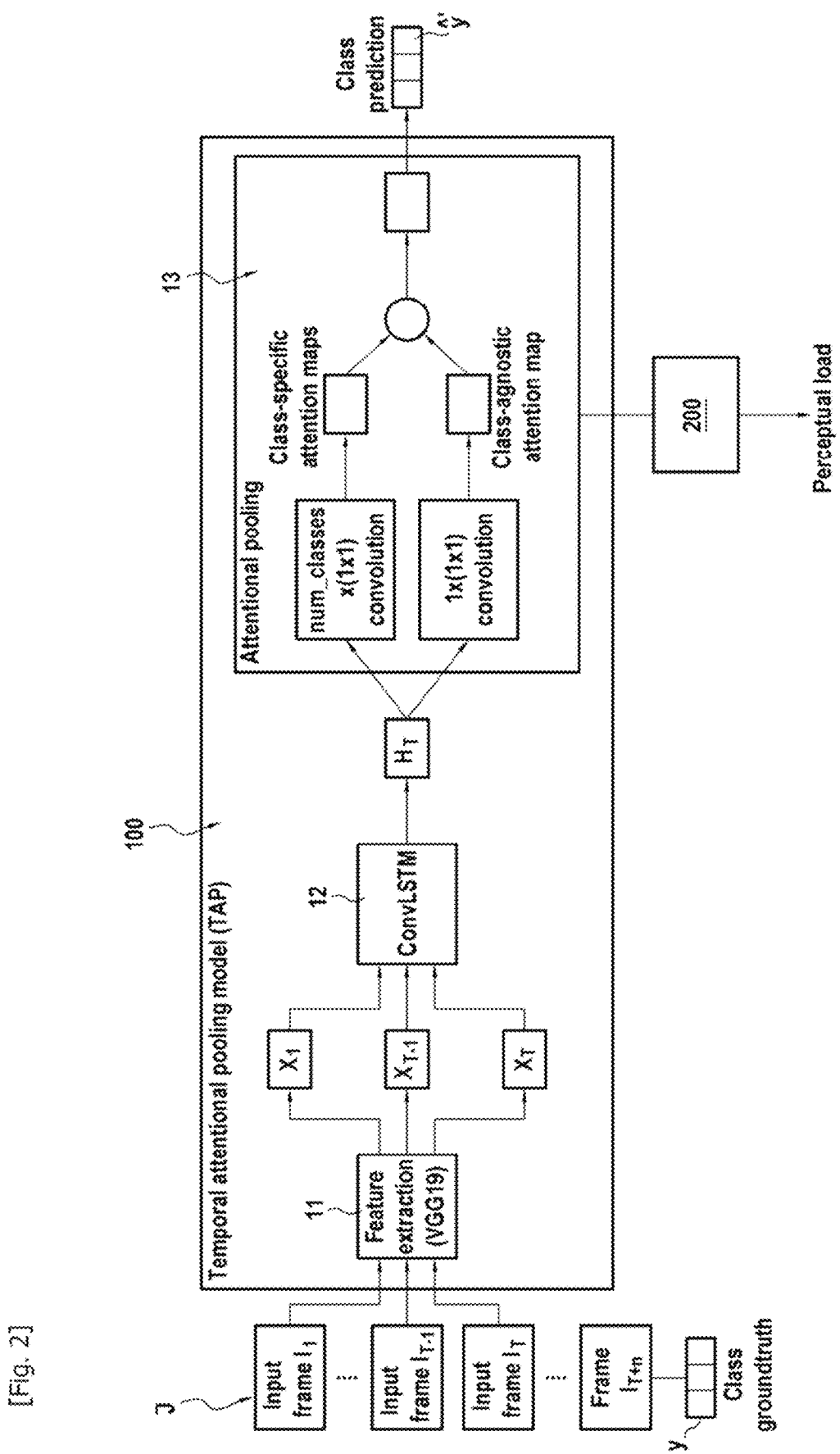

[Fig. 3]
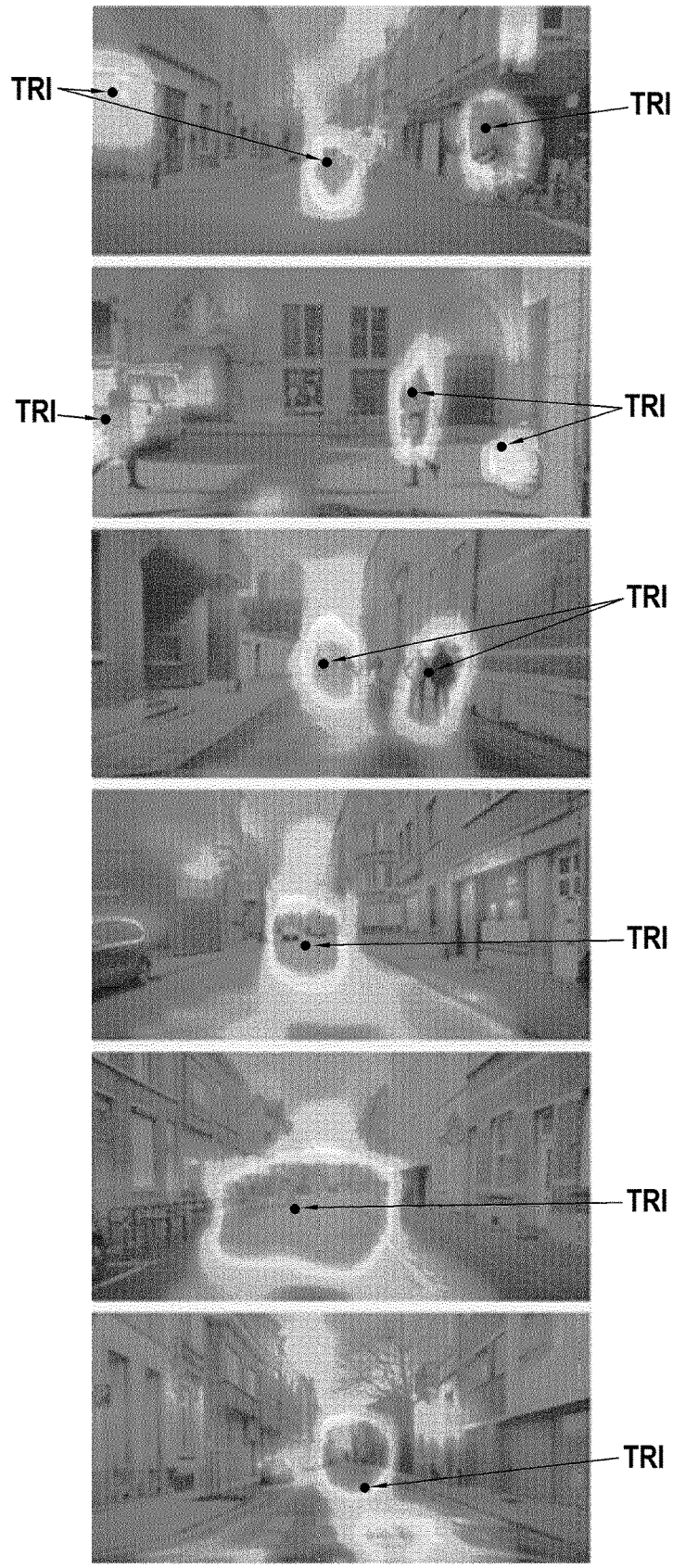

CONTROL DEVICE, SYSTEM AND METHOD FOR DETERMINING PERCEPTUAL LOAD OF A VISUAL AND DYNAMIC DRIVING SCENE IN REAL TIME

FIELD OF THE DISCLOSURE

The present disclosure is related to a control device, system and method for a vehicle for determining perceptual load (i.e. attentional demand) of a visual and dynamic driving scene, in particular of an uncontrolled, dynamically changing visual scene that the driver (or any automated driving system) must perceive to carry out the driving task.

BACKGROUND OF THE DISCLOSURE

The ability to recognise perceptual load of the uncontrollable dynamic visual environment in which vehicles are driven and changes hereof including sudden surges, could significantly improve driving safety by providing the basis for new designs and strategies for use of warning signals. It could also set a standard against which the usefulness of other measures of detecting driver attention and engagement can be assessed, e.g. physiological measures such as pupil or EEG measurements. Further it could also apply to designing optimum strategies for vehicle-to-driver interactions for highly automated vehicles, for example but not limited to the case of so-called take-over-requests, where the automatic control system requests a driver to re-take control over vehicle operation. Further, it could also apply to designing control strategies for the automated controller based on driver model considering the different modalities of for example "cautious driver", "normal driver", "sporty driver".

Methods are known which model safety critical events after they have occurred, i.e. once the driver e.g. steers or brakes to avoid a collision.

However, it remains desirable to anticipate critical events by considering one of the root causes—inattention due to the level of information load from the visual scene. For example, it is well established in cognitive neuroscience that the amount of load on the brain is critical to determining whether a task can be fully perceived, with high levels of perceptual load causing inattentional blindness—a phenomenon where a person looks but "fails to see". This can have serious consequences in driving, where failing to notice changes in the visual environment can result in accidents. On the other hand very low levels of load may imply the risk that the driver's concentration deteriorates.

Numerous laboratory studies have looked at the effect of load on performing laboratory tasks of attention (for example visual search), as e.g.:
  Lavie, N. and Cox, S. (1997): "On the efficiency of visual selective attention: Efficient visual search leads to inefficient distractor rejection", Psychological Science, 8(5):395-396,
  Beck, D. M. and Lavie, N. (2005): "Look here but ignore what you see: Effects of distractors at fixation", Journal of Experimental Psychology: Human Perception and Performance, 31(3):592-607,
  Cartwright-Finch, U. and Lavie, N. (2007): "The role of perceptual load in inattentional blindness", Cognition, 102(3):321-340, or
  Roper, Z. J. J., Cosman, J. D., and Vecera, S. P. (2013): "Perceptual load corresponds with factors known to influence visual search", Journal of Experimental Psychology: Human Perception and Performance, 39(5): 1340-1351.

A few studies also tested the effects of laboratory manipulations of perceptual load on people's performance of a driving simulator task, as e.g.:
  Marciano, H., and Yeshurun, Y. (2011). "The effects of perceptual load in central and peripheral regions of the visual field". Vis. Cogn. 19, 367-391. doi: 10.1080/ 13506285. 2010.537711,
  Marciano, H., and Yeshurun, Y. "Perceptual load in central and peripheral regions and its effects on driving performance: Advertizing billboards", Work: A Journal of Prevention, Assessment and Rehabilitation, 2012, 41, 3181-3188,
  Redenbo, S. J., and Lee, Y. C. (2009). "Effects of cognitive and perceptual loads on driver behavior". Transportation Research Record, 2138, 20-27, and
  Tan, P. H., and Lee, Y. C. (2009). "Effect of perceptual and cognitive loads on drivers' attention and resistance to distractors". In Proceedings of the Human Factors and Ergonomics Society 53rd Annual Meeting (pp. 1739-1743). Santa Monica, CA: Human Factors and Ergonomics Society.

A number of approaches have been used for estimating general driver load (known as workload) including:
  Subjective measures such as through self-report and self-rating scales;
  Physiological measures including measures of brain activity (e.g. task-related brain potentials which can be sensed through EEG), heart activity (e.g. heart rate), eye activity (e.g. pupil dilation and blink rate), and stress activity (e.g. through galvanic skin response);
  Task and performance-based measures such as reaction times and error rates;
  Behavioural measures such as speech disfluencies.

Girdhar et. al. proposess using attention mechanism in a neural network for recognising human actions in a video, cf.:
  Rohit Girdhar and Deva Ramanan: Attentional pooling for action recognition. In Advances in Neural Information Processing Systems, pages 34-45, 2017.

The proposed attentional pooling network parameterises a weight for each location in the feature map as a 1×1 convolution of the previous feature map. This simple addition leads to an RGB-only action recognition, while also producing sensible and interpretable explanations for network decisions.

Kim et. al. proposes using an attention mechanism in driving to identify objects/location of the scene which affected the driving control, cf.:
  Jinkyu Kim and John F Canny. Interpretable learning for self-driving cars by visualizing causal attention. In ICCV, pages 2961-2969, 2017.

The output of the mechanism is used to guide and prune an occlusion-based visualisation method to determine explanatory scene regions for model behaviour.

WO2017211395 (A1) discloses a method for determining perceptual load based on subjective estimates obtained in crowd-sourcing. It thus relies on the subjective assessment of perceptual load by people viewing e.g. dash-cam videos of driving scenarios.

SUMMARY OF THE DISCLOSURE

Currently, it remains desirable to provide a control device and method for determining perceptual load of driving directly from the visual driving scene, without the need of relying on subjective estimates obtained in crowd-sourcing. More in particular it remains desirable to provide a control device and method for detecting temporal and spatial portions of the driving scene which imply an increased perceptual load.

The invention resolves these issues by determining perceptual load of a driving scene (or at least an estimate of said perceptual load) directly from the driving scene surrounding the vehicle and optionally on the basis of driver driving-task behavior (as expressed in the driving controls). The determination may thus be done in real-time or at least quasi real-time.

Therefore, according to the embodiments of the present disclosure, a control device for a vehicle for determining perceptual load of a visual and dynamic driving scene is provided. The control device being configured to:
- receive an image sequence representing the driving scene,
- extract a set of scene features from the image sequence, the set of scene features representing static and/or dynamic information of the driving scene,
- calculate a time-aggregated representation of the image sequence based on the extracted set of scene features,
- calculate an attention map of the driving scene by attentional pooling of the time-aggregated representation of the image sequence, and
- determine the perceptual load of the driving scene based on the attention map.

Accordingly, the control device allows to measure and predict the perceptual load of a dynamic driving scene from mapping within-model attention heatmaps onto perceptual load levels that predict and correlate with human subjective ratings of perceptual load. This may be done in real-time or at least quasi real-time.

By providing such a control device, real-world driving telemetry (e.g. speed, yaw etc.) may be used to train a (driving) model that produces car-control signals for a given visual input of the scene. This model contains a submodule which prioritises certain parts of the visual scene over others (i.e. an 'attention mechanism'). Activations in this module are transformed to estimate perceptual load, using principles from the cognitive science literature (cf. e.g. Nilli Lavie. Attention, distraction, and cognitive control under load. Current directions in psychological science, 19(3):143-148, 2010). In this way it measures perceptual load that is directly shown to relate to driving behaviour. This is an advantage over previous methods to estimate perceptual load during driving that only rely on the subjective assessment of perceptual load by people viewing dash-cam videos of driving scenarios. Driving behaviour for example slowing down, braking or steering away from an oncoming road object (e.g. vehicles, pedestrians etc.) is an inherently valid measure of the relevance of a road object to driver attention.

Another advantage of the control device of the present disclosure is that it is able to produce estimates of perceptual load using e.g. readily available telemetry data, rather than requiring time-consuming video labelling, especially suitable for dynamic driving scenes where "action-reaction paradigm" is of great importance.

Nevertheless, although the control device desirably uses driving telemetry, it may also be expanded to use other input to produce attention maps that are transformed to perceptual load levels (for example, eye gaze patterns).

In general the control device may comprise two modules: 1) an attention mechanism (provided e.g. by a driving model) which estimates the importance of visual information across the scene, in terms of its relevance to the task of driving, and produces an attention 'heatmap' or 'distribution'; and 2) a process (e.g. provided by an algorithm or by a load model) for mapping this spatial attention distribution to a single value which represents the perceptual load of the scene.

The perceptual load of a visual and dynamic driving scene may also be referred to as the attentional demand implied by a visual and dynamic driving scene. In the cognitive science literature (cf. e.g. Nilli Lavie. Attention, distraction, and cognitive control under load. Current directions in psychological science, 19(3):143-148, 2010), the perceptual load of a task (e.g. for a driver perceiving a driving scene) is operationally defined in terms of the number and relevance of the visual 'items' it is necessary to perceive in order to complete the task (e.g. the driving task). Here, these are named task-relevant items (TRIs), and such items may or may not be 'objects' in the normal sense.

It is still noted that the control device is at least configured to determine an estimate of the, i.e. a determined or calculated value, representing the perceptual load of the driving scene.

The driving scene may represent a visual scene seen from the driver's seat in vehicle front direction (i.e. corresponding to a "subjective" driver's gaze direction when driving). The driving scene may therefore comprise information regarding the environment of the vehicle, in particular in front of the (moving) vehicle, and desirably also of the vehicle's maneuvers. For example, in case the vehicle turns to left and brakes, this has an effect to the field of view and dynamics of said driving scene.

The control device may also be referred to as an electronic device.

The attention map may comprise for each image of the sequence a heat map representing a spatial attention intensity distribution across the image.

The perceptual load of an image may be determined based on the heat map of said image.

Determining the perceptual load may comprise determining at least one spatial and/or temporal peak area of increased attention in the driving scene.

For example, said determination may be made in combination with determining a contribution value of said peak area to a total value of the perceptual load.

Desirably, the peak area may represent a task relevant item (TRI).

Determining the at least one peak area may comprise threshold-segmenting a heat map, for example each heat map of the driving scene, to isolate contiguous pixel regions of increased attention.

Determining the at least one peak area may comprise normalizing a heat map, in particular each heat map of the driving scene, to produce a discrete probability distribution, and unsupervised clustering, e.g. by an iterative Gaussian mixture model (GMM), the discrete probability distribution to identify cluster centers of the pixel clusters of increased attention.

Determining the contribution value of a peak area to the total value of the perceptual load may comprise identifying the pixel or neighborhood of pixels which has the highest attention value within the peak area, and determining the perceptual load value based on said highest attention value.

Determining the perceptual load value of a scene may comprise calculating the sum of perceptual load contribution values of the peak areas comprised by the driving scene, e.g. including a weighting of the contribution values based on the locations of the peak areas and/or based on a predetermined classification of the peak areas.

The control device may comprise a driving model trained to predict driving maneuvers. Said model may be e.g. a temporal attentional pooling model.

The driving model may be trained (to predict the driving maneuvers) based on training image sequences representing driving scenes.

Each of the training image sequences may represent a driving scene and may optionally be labelled in addition with respective human driving maneuvers carried out during the driving scene.

The control device may be further configured to receive information regarding driving maneuvers carried out by the vehicle driver during the driving scene (e.g. extracted from the steering control system, e.g. a CAN bus, of the vehicle or directly from the visual and dynamic driving scene), and determine based on said information and the determined perceptual load whether the driver is attentive to the driving scene.

The control device, desirably the driving model, comprises at least one of a first neural network, e.g. a convolutional neural network (CNN), for extracting the set of scene features, a second neural network, e.g. a convolutional long short-term memory network (Conv-LSTM), for calculating the time-aggregated representation of the image sequence, an attentional pooling mechanism for calculating the attention map, and optionally an algorithm for determining the perceptual load of the driving scene based on the attention map.

The algorithm may also be comprised by the control device but be external to the driving model.

The control device may comprise a trained load model configured to determine the perceptual load of the driving scene based on the attention map.

The disclosure may further relate to a vehicle comprising a control device as described above.

The vehicle may further comprise at least one sensor configured to sense the visual driving scene, The at least one sensor may provide or output the image sequence representing the visual driving scene.

The sensor may be comprise in particular at least one optical sensor, more in particular at least one digital camera. Alternatively or in addition the sensor(s) may comprise at least one Lidar Sensor, and/or at least one radar sensor.

Accordingly, also a plurality of sensors may be used, in order to sense (i.e. perceive) the driving scene. For example, two sensors might be used, in order to obtain three dimensional information of the driving scene, as well as surround view type sensor configuration, and any combination hereof.

The vehicle may be configured for a at least partially automated driving control. The control device may be used in a pre-processing step of the driving control to identify portions with increased perceptual load in the sensed driving scene based on which the automated driving is controlled.

The vehicle may comprise hardware and/or software resources configured for the at least partially automated driving control.

Said hardware and/or software resources may be allocated to process the portions with increased perceptual load in prioritized manner.

Accordingly, the portions of the sensed driving scene implying an increased perceptual load (when compared to the other portions of the same driving scene implying a lower perceptual load) may be processed (i.e. considered) first. In this way the (limited) hardware and/or software resources may be used efficiently. Of course, the prioritized processing of portions with increased perceptual load does not imply that other portions are not processed at all.

However, these other portions may be processed with a lower priority, e.g. with regard to processing time and/or used processing power.

The vehicle may comprise a human-machine-interface configured to output to human the portions with increased perceptual load. Accordingly, the human-machine-interface may contribute to a safe driving of the driver. For example, the human-machine-interface may mark the portions with increased perceptual load but may alternatively or additionally also highlight other regions in the sensed driving scene. Hence, such other regions which may also be relevant for safe driving may be drawn to the attention of the driver who otherwise might disregard them. Additionally or alternatively, the human-machine-interface may be configured for so-called take-over-requests, where the automatic control system requests a driver to re-take control over vehicle operation. In such situations it is important for the automatic control system to be able to reliably determine the perceptual load of the driving scene related to the driving task. A further exemplary configuration would be that the automatic control system takes over driving control, e.g. in case the system recognizes that the determined perceptual load exceeds a specific threshold.

The present disclosure further relates to a method of determining perceptual load of a visual and dynamic driving scene, comprising the steps of:

a—training a prediction model what includes training a temporal attentional pooling model comprising an attentional pooling mechanism in a supervised manner by using a set of training image sequences, each of said sequences representing a visual and dynamic driving scene and being labelled with respective human driving maneuvers carried out during the driving scene, and b—inputting a test image sequence representing an unknown visual and dynamic driving scene into the trained model, c—obtaining an attention map from the trained attentional pooling mechanism in response to the inputted test image sequence, d—determining the perceptual load of the unknown driving scene based on the attention map.

The prediction model may consist of the driving model described above or it may comprise further elements, e.g. a load model, as described below.

The step of obtaining an attention map may further comprise the steps of:

c1—extracting a set of scene features from the test image sequence, the set of scene features representing static and/or dynamic information of the unknown driving scene and of the vehicle, c2—calculating a time-aggregated representation of the test image sequence based on the extracted set of scene features, and c3—calculating the attention map of the unknown driving scene by attentional pooling of the time-aggregated representation of the test image sequence.

The step of training the temporal attentional pooling model may further comprise the steps of:

a1—obtaining a set of training image sequences, each sequence representing a driving scene performed by a human driven vehicle, a2—obtaining a data set of human driving maneuvers carried out during the driving scenes, a3—training the model in a supervised end-to-end learning manner to learn predicting driving maneuvers by using the set of training image sequences being labelled with the respective human driving maneuvers.

The prediction model may further comprise a load model, the step of training the prediction model comprising the further steps of:

a4—obtaining a data set of human generated load labels assigned to the human driving maneuvers carried out during the driving scenes, a5—training the load model for predicting the perceptual load of a visual and dynamic driving scene based on the output of the trained attentional pooling mechanism and the human generated load labels, wherein the load model is in particular trained together with the driving model in an end-to-end-manner. Human generated load labels may be generated by a sensor, e.g. at least one functional near-infrared spectroscopy (fNIRS) sensor device. The sensor may be configured to measure the working memory load at the frontal cortex of the human.

Accordingly, Variants of the method may also incorporate extra supervision during the machine learning phase (e.g. in the form of human ratings of load, or associated physiological measurements) to produce more accurate perceptual load estimation networks. This may be achieved through implementing (i.e. training) a second part (i.e. a load model) of the prediction model (i.e. mapping attention distribution to perceptual load) as a differentiable perceptual load model and back-propagating load prediction errors during end-to-end training. This allows extra human supervision, in the form of subjective labels or physiological signals indicative of perceptual load, to be introduced to guide the model towards more human-like attention distributions and perceptual load predictions.

It is intended that combinations of the above-described elements and those within the specification may be made, except where otherwise contradictory.

It is to be understood that both the foregoing general description and the following detailed description are exemplary and explanatory only and are not restrictive of the disclosure, as claimed.

The accompanying drawings, which are incorporated in and constitute a part of this specification, illustrate embodiments of the disclosure and together with the description, and serve to explain the principles thereof.

BRIEF DESCRIPTION OF THE DRAWINGS

FIG. 1 shows a block diagram of a system with a control device according to embodiments of the present disclosure;

FIG. 2 shows a representation of a driving model which can be used as a basis for estimating the perceptual load according to embodiments of the present disclosure; and FIG. 3 shows examples of heat maps and calculated peak areas (i.e. TRIs) of perceptual load in single images (i.e. video frames) according to embodiments of the present disclosure.

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts.

FIG. 1 shows a block diagram of a system 30 with a control device 1 according to embodiments of the present disclosure.

The control device 1 is connected to or comprises data storage 2. Said data storage may be used to store e.g. the trained driving model, e.g. a temporal attentional pooling model, and/or an algorithm for calculating an estimated perceptual load of the driving scene based on the predicted attention map. Said algorithm may eventually also comprise a trained load model. As described in the following, said driving model and the algorithm are used to calculate an estimated perceptual load of a visual driving scene.

The control device 1 may additionally carry out further functions in the vehicle 10. For example, the control device may also act as the general purpose ECU (electronic control unit) of the vehicle. The control device 1 may comprise an electronic circuit, a processor (shared, dedicated, or group), a combinational logic circuit, a memory that executes one or more software programs, and/or other suitable components that provide the described functionality.

The control device 1 may further be connected to at least one sensor, in particular a digital camera 3. Alternatively or in addition the sensor(s) 3 may comprise at least one Lidar Sensor, and/or at least one radar sensor.

The control device 1 and the sensor may be comprised by a vehicle 10. The sensor 3 is configured such that it can record a visual driving scene of the vehicle 10. The sensor is desirably oriented in the driving direction of the vehicle, i.e. such that it records in particular the road in front of the vehicle. It is also possible to use sensors, e.g. in order to cover the complete field of view of the driver.

The output of the sensor 3, in particular a recorded video stream, is transmitted to the control device 1. Desirably, the output is transmitted instantaneously, i.e. in real time or in quasi real time. Hence, the perceptual load of the recorded driving scene can also be determined by the control device in real time or in quasi real time.

The system 30 may comprise additionally a server 20. The server 20 is used to train and eventually update the driving model and/or load model. For this purpose, the control device 1 may be connectable to the server. For example the control device 1 may be connected to the server 20 via a wireless connection. Alternatively or additionally the control device 1 may be connectable to the server 20 via a fixed connection, e.g. via a cable.

Again with reference to the control device 1, said control device 1 desirably comprises two modules: 1) an attention mechanism (provided by the driving model) which estimates the importance of visual information across the scene, in terms of its relevance to the task of driving, and produces an attention 'heatmap' or 'distribution'; and 2) a process (provided by the algorithm) for mapping this spatial attention distribution to a single value which represents the perceptual load of the scene.

Accordingly, the control device is configured to measure and predict the perceptual load of a dynamic driving scene from mapping within-model attention heatmaps onto perceptual load levels that predict and correlate with human subjective ratings of perceptual load. The driving model that includes the attention heatmaps can be a model predictive of driving control behaviour in the form of an end-to-end neural network (as described in the following and also in context of FIG. 2) or it could be based on other driver attention estimation models (for example on the basis of eye gaze pattern), or any combination hereof.

The prediction of the perceptual load level may be used as a base of driver assistive warning system (e.g. in levels 0-3 of HAD (highly automated driving)) whereby e.g. a warning signal is sent when the perceptual load level has reached a predefined threshold for example in level 0 a warning can be sent to the driver to indicate that they should now pay full attention to the road. It may also warn the other car occupants to not distract the driver. In this context it is noted that driver distraction from interacting with car occupants can increase crash probability 12 times more than mobile phone distraction. On the other hand, it has been speculated that a reason for handsfree operation of the vehicle does not eliminate the risk of lacking understanding of the dynamic driving scene wherefore the person at the other end will continue talking even as the driving situation may suddenly demand the full attention of the driver. Either way technical advantages are clear (by warning of person in the other end, by muting etc). Warning signals may also alert driver to be prepared that a high load/attention demanding events are more probable at certain scenarios (e.g. that the driving environment can present a state of increased load). These could be pre-warning signals as the model can predict the attention demanding events and location before they are apparent to the driver.

The control device 1 may also inform a TOR (take over request) design in relation to the level of perceptual load (e.g. a TOR can be tailored to be earlier, of greater intensity or involving more sensory modalities as perceptual load is increased). Alternatively the control device would have greater readiness to take over from the driver with increased levels of perceptual load (passing a threshold). Machine learning networks may also benefit from said prediction of the overall level of perceptual load in training as data sampling tool, i.e. a determined increase of perceptual load may be interpreted as the provision of more informative data.

The control device 1 may also be used for training of autonomous driving systems, as it allows the estimation of a useful, and hitherto unleveraged, dimension of the driving task itself: the perceptual load of the driving environment. For example, to improve the performance of an autonomous driving model in high-load scenarios (e.g. dense urban environment with many vehicles and pedestrians in motion etc.), the loss-contribution of examples during training may be weighted by perceptual load such that there is a greater penalty associated with incorrect driving decisions in these situations. Similarly, the estimated perceptual load level may be used to subsample a dataset according to perceptual load—a model could be trained on a high-load subset of data such that its driving ability in these situations is increased. Bias in a driving model across this dimension could become especially useful in a 'Guardian' view of semi-autonomous driving, where the driving system is likely to be engaged exactly where humans are likely to fail (i.e. in situations of high perceptual load).

As noted before, an integral component of the control device 1 is a (driving) model or system which produces an 'attention heatmap' of the driving scene, which is analogous to a distribution of the importance to driving control behaviour of different parts (locations) of the driving scene. For example, a pedestrian shaping up to cross the road will be more important than a pedestrian walking on the pavement towards a shop entrance.

There are several ways to provide these attention maps. For example, these heatmaps might also be produced by inspecting a neural network trained to drive in an autonomous fashion (i.e. a system which takes in sensor readings from the environment and produces signals used to control the vehicle). Given such a trained model one could (in repeated simulations) occlude certain regions of the scene and measure how much the predicted control signal is affected; regions which, when removed from the input, degrade the car control signal can be seen as important to the driving situation, and a heatmap could be built by this process being repeated across the whole scene.

Another desirable method (detailed in context of FIG. 2) is instead to imbue an autonomous driving model with a simulated attention mechanism, allowing the model to prioritise certain regions of the environment for further processing, in analogy with the human capacity for attention. In this setting, a deep neural network is trained to produce car control signals: a large dataset of (input, output) pairs is constructed, and the network learns to produce the outputs when presented with the inputs. The inputs to the network are sensor recordings of the state of the environment (e.g. cameras, LIDAR, telemetry, driver physiology in the semi-autonomous sphere), while the target outputs are telemetry readings of the car's control signals (e.g. steering angle, brake depression) slightly into the future.

By approximating the true car control of the driver, the model can be seen to be learning the task of driving. For example, when fed with novel sensor readings from the environment, the system can produce human-like control signals in real-time (e.g. slow-down by 0.5 m/s and turn left 4 degrees). An example structure of a neural network designed for this task would be a 'perceptual' system which extracts visual features of each frame, e.g. a convolutional neural network (CNN), in conjunction with a module for temporal integration (e.g. a convolutional LSTM) which acts to extract and collate visual information across time, followed by fully-connected layers which transform the data into a few outputs which correspond to the car control signals.

Importantly, a spatial attention mechanism may be placed into the network such that spatial features of an incoming frame are weighted according to their importance for producing correct car controls. The weights of the spatial attention map may be calculated by a learned convolution of a feature tensor constructed by concatenating the incoming frame feature tensor with a hidden state tensor. In this way, the attention mechanism is conditional on the current input as well as the recent visual history as encoded by the temporal integration module. After the attentive driving model is trained, streaming sensor data, and/or novel video of a driving scenario can be fed as input and the model will produce driving control signals, and more importantly, an attention distribution across the visual field.

In addition, human eye-positions may be recorded during driving and train a model to replicate these eye movements, by framing human eye-position as an indicator of scene importance, the model can highlight gaze-important regions of the driving scene, i.e. produce an attention heatmap across the scene (e.g. Pallazzi et al., Learning where to attend like a human driver, 2017 IEEE Intelligent Vehicles Symposium (IV), Pages 920-925). To the extent that fixation positions represent driver attention this might be used in addition to estimate (or check) perceptual load.

FIG. 2 shows a representation of a driving model which can be used as a basis for predicting the perceptual load according to embodiments of the present disclosure.

The driving model principally comprises a network to predict driving commands based on an image sequence representing the visual driving scene, e.g. a front-facing video input of one or several cameras of the vehicle. The driving model thereby has an end-to-end driving architecture that includes a spatial attention mechanism allowing the prioritisation of visual information.

The driving model 100 is in particular a temporal attentional pooling (TAP) model. An input sequence I of the TAP model 100 is first passed through a feature extraction network 11 and the resulting features are then processed by a ConvLSTM 12 (i.e. a convolutional Long short-term memory network) which outputs a time-aggregated representation of the whole sequence. This representation then goes through attentional pooling 13, which predicts the label 9 for the shown sequence. The class-agnostic attention map is what later may be used for estimating the attentional demand of the driving scene.

This driving model is trained desirably only with readily-available vehicle odometry data y, i.e. without any subjective estimates obtained in crowd-sourcing. In other words it is trained with a data set of human driving maneuvers carried out during the driving scenes. An algorithm 200 may be used which processes the network's internal attentional state, e.g. according to an operational cognitive model of perceptual load, i.e. attentional demand. This algorithm allows the real-time estimation of scene difficulty during driving using only the image sequence representing the visual driving scene.

The driving model 100, its training procedure, and the algorithm 200 are described in the following in more detail:

Given a sequence of images $\mathcal{J} = \{I_1, \ldots, I_T\}$ and a ground truth label y assigned to the whole sequence, a model may be developed which predicts the label $\hat{y}$ for the given sequence, while also providing a way of interpreting which parts of the input were important in making that prediction. To this endit is proposed extending the attentional pooling method of module 13 (cf. e.g. Rohit Girdhar and Deva Ramanan: Attentional pooling for action recognition. In Advances in Neural Information Processing Systems, pages 34-45, 2017) to the temporal domain using a convolutional LSTM, and so define an architecture which is called temporal attentional pooling (TAP). The TAP architecture consists of three components: a perceptual component 11 for extracting frame-based visual representations (VGG19, cf. e.g. Karen Simonyan and Andrew Zisserman. Very deep convolutional networks for large-scale image recognition. arXiv preprint arXiv:1409.1556, 2014), followed by temporal integration component 12—e.g. e a convolutional LSTM to maintain the spatial structure of the data (ConvLSTM, cf. e.g. SHI Xingjian, Zhourong Chen, Hao Wang, Dit-Yan Yeung, Wai-Kin Wong, and Wang-chun Woo. Convolutional LSTM network: A machine learning approach for precipitation nowcasting. In Advances in neural information processing systems, pages 802-810, 2015), and finally an attention mechanism component 13 to prioritise certain regions of the input.

The ConvLSTM is an extension of the LSTM model which can be used to extract a representation of a sequence including a spatial structure. The main parts of the ConvLSTM are its two internal states: the hidden state H and the cell state C; and the gates which control how the internal states are modified: the input gate i, the forget gate f, and the output gate o. The value of a gate or a state variable at a certain time step is denoted by including a subscript t, i.e. the cell state C at time t is denoted as $C_t$ and the hidden state at the previous time step is $H_{t-1}$. Given a 3D tensor $X_t$ as the input at time step t, all of the internal gates and states are updated according to the following equations:

$$i_t = \sigma(W_{xi} * X_t + W_{hi} * H_{t-1} + b_i) \quad (1)$$

$$f_t = \sigma(W_{xf} * X_t + W_{hf} * H_{t-1} + b_f) \quad (2)$$

$$o_t = \sigma(W_{xo} * X_t + W_{ho} * H_{t-1} + b_o) \quad (3)$$

$$C_t = f_t \odot C_{t-1} + i_t \odot \tan h(W_{xc} * X_t + W_{hc} * H_{t-1} + b_c) \quad (4)$$

$$H_t = o_t \odot \tan h(C_t) \quad (5)$$

where $\sigma$ denotes the sigmoid function, * is the convolution operator, $\odot$ denotes the Hadamard product, $W_*$ are the filter weights used in the convolutions, and $b_*$ are the biases. The cell state C is not included when calculating the gate activations, i.e. peephole connections are not used.

The hidden state $H_t$ and the cell state $C_t$, as well as the input $X_t$ are 3D tensors with equal trailing two dimensions. The number of channels in H and C is equal and is set arbitrarily as a hyperparameter of the model, while the number of channels of X depends on the choice of the feature extraction model used for processing the input images, i.e. $X_t = FE(I_t)$, where it is used FE to denote a convolutional network, such as VGG19 with its fully connected layers removed. The output of the ConvLSTM model is the value of its hidden state $H_T$, i.e. the hidden state at the last time step, after the whole sequence $\mathcal{J}$ has been processed. $H_T$ can be interpreted as a representation of the whole sequence, and it may be fed into the final part of TAP, which is the classification module with an attention mechanism.

The output of the ConvLSTM is a spatial feature map to which it is applied an attentional pooling decision layer to predict the target label. Scores for each class are calculated as inner products of two attentional heatmaps; a class-dependent heatmap representing which parts of the input are indicative of a particular class, and the class-independent heatmap representing which parts are important for classifying the given sample in general. More formally, the score of a sample M belonging to class k can be written as:

$$score(M,k) = (Ma_k)^T (ReLu(Mb)), \quad (6)$$

where M is used to denote a 3D tensor (in our case the tensor $H_T$) viewed as a matrix of shape (n×ch), with n being the number of spatial locations in the tensor and ch the number of its channels. The vectors $a_k$ and b denote the class-specific and class-agnostic weights, respectively. Reshaping the product Mb into a matrix of the same size as the spatial size of the tensor $H_T$ results in a heatmap which can be interpreted as a distribution of importance across space. Note that the class-agnostic heatmap is passed through a ReLu activation function otherwise a negative value in the class-agnostic heatmap would not necessarily mean that the feature at that location is unimportant (since the class-dependent attention values can take on negative values). In this following an example of an algorithm 200 for predicting the perceptual load is described.

In the cognitive science literature (cf. e.g. Nilli Lavie. Attention, distraction, and cognitive control under load. Current directions in psychological science, 19(3):143-148, 2010), the perceptual load of a task is operationally defined in terms of the number and relevance of the visual 'items' it is necessary to perceive in order to complete the task. Here these are named task-relevant items (TRIs), and such items may or may not be 'objects' in the normal sense.

FIG. 3 shows examples of heat maps and calculated peak areas (i.e. TRIs) of perceptual load in single images (i.e. video frames) according to embodiments of the present disclosure.

To identify such TRIs at test time using a trained TAP driving model, the class-agnostic attention map is interpreted at identifying regions important for completing the task (i.e. for producing the correct driving control). To identify TRIs from the produced pixel-level attention map, the map is threshold-segmented to isolate contiguous regions of highly relevant pixels. The threshold may be set at 1, which is indicative of the attentive driving model amplifying the features describing this pixel region. Contiguous positive regions of this binary map are identified as TRIs where each TRI is represented as a set of pixel coordinates. The attentional demand contribution of each TRI is calculated as the maximum attention value within the TRI. The overall attentional demand of a scene is then the sum of the contributions of each TRI. An example of the algorithm for calculating the attentional demand (i.e. perceptual load) is shown in the following:

| Algorithm 1 Algorithm for calculating demand from attention map. |
|---|
| 1. function CALCULATE_DEMAND(att) |
| 2:     bin_att ← zeros_like(att)     ▷ initialise a zero array of same shape as att |
| 3:     bin_att[att ≥ 1] ← 1     ▷ create binary attention mask |
| 4:     TRIs ← connected_components(bin_att)     ▷ find the set of TRIs |
| 5:     total_demand ← 0     ▷ initialise output |
| 6:     for each TRI ∈ TRIs do     ▷ each TRI is a set of pixels |
| 7:         att_value ← 0 |
| 8:         for each p ∈ TRI do |
| 9:             att_value ← max (att_value, att [p])     ▷ find max value in att map |
| 10:         total_demand ← total_demand + att_value     ▷ increment total demand value |
| 11:     return total_demand |

Training the Driving Model:

To train the end-to-end attentive driving model a dataset may be used, which contains e.g. 100 hours of video footage collected from e.g. five cameras (front center, front wide, left wide, right wide, rear wide) mounted on a car. The car may be equipped with a global positioning system (GPS) and an inertial measurement unit (IMU) collecting e.g. at least one of the following sensor data: latitude, longitude, altitude, speed, roll, pitch, yaw, roll rate, pitch rate, yaw rate, forward acceleration, lateral acceleration, and vertical acceleration. Each sensor data stream may be linearly interpolated to provide ground-truth values associated with each camera frame. It is though also possible to use only the video data recorded from the center front-facing RGB camera as input to the driving model, collected at e.g. 10 frames per second at a resolution of e.g. 640×1280 pixels.

In the following it is described how the proposed TAP model may be trained. At first a simple car control task may be defined; given a sequence of T frames $\mathcal{J} = \{I_1, \ldots, I_T\}$ from a driving video (i.e. video taken from a front-facing camera mounted on a car), predict whether the driver should accelerate, decelerate or continue driving at constant speed at time step T+n. As the acceleration values $a_t$ are known for each video frame, the ground truth label y may be generated for a selected sequence by simply binning the acceleration value a at time step T+n into one of three predefined value ranges. In this example the driving decision for a sequence may be labeled as 'decelerate' if $a_{T+n} < -0.3$ m/s$^2$, 'accelerate' if $a_{T+n} > 0.3$ m/s$^2$, and 'constant' for other values. It may be set T=12 and n=24, meaning that the input sequence consists of 12 frames and its corresponding label comes from 24 frames in the future. Taking the video sampling rate into account (10 FPS), the length of the input sequence is 1.2 seconds long, and the driving control which is to be predicted is from 2.4 seconds in the future.

Each of the frames $I_t$ (resized to e.g. 224×448 pixels) may be processed in the input sequence by passing them through a feature extraction network; in this example the convolutional layers of VGG19 are used with the last pooling layer removed as the feature extraction network. The network is pre-trained on e.g. the ImageNet dataset. The extracted feature maps $X_t$ (e.g. having 512 channels and a spatial size of 14×28 pixels) are then fed into the convLSTM sequence feature extraction module described before, and the resulting representation is used as the input to the attentional pooling module which gave the label prediction at its output. The number of hidden channels in the convLSTM used is set to e.g. 128. Each of the convolutional filters $W_*$ in the convLSTM were of size 1×1 px. The entire TAP network is trained end-to-end for a total of 200 epochs by minimising cross-entropy loss with stochastic gradient descent with momentum (m=0.9) with a learning rate of 0.01 and training batch size 24. The learning rate is divided by 2 halfway throughout the training. The total number of parameters in the network is 20.3 M. One epoch consists of showing 2496 samples from the training set.

In summary, the crux of the proposed method carried out by the control device is to process the attention map according to principles in cognitive science to produce an estimate of 'attentional demand' or 'perceptual load' on the driver due to the dynamic traffic scene. In the cognitive science literature (e.g. Lavie et. al. as cited above), the perceptual load of a task is operationally defined in terms of the number and relevance of the visual 'items' it is necessary to perceive in order to complete the task. These may be named task-relevant items (TRIs), and such items may or may not be 'objects' in the normal sense. The contribution of each TRI to the overall perceptual load of the traffic scene can be seen as equivalent to the value of the attention map at the centre-of-mass of the TRI, and the overall perceptual load of the scene is then the sum of the contributions of each TRI in the scene.

To identify TRIs from the pixel-level relevance map that the attention mechanism produces several methods may be applied, for example:

As described above in context of FIG. 2, as "threshold and identify" method may be applied. In this case the attention map is threshold-segmented to isolate contiguous regions of highly relevant pixels. The threshold is set at e.g. 1, which is indicative of the attentive driving model amplifying the features describing this pixel region (i.e. the model assesses that this region contains information relevant for the driving control decision). Contiguous positive regions of the map after thresholding are identified as TRIs; each TRI is therefore represented as a set of pixel coordinates, {p0 . . . pN}, where N is the number of pixels in the TRI. The perceptual load contribution of each TRI is first calculated as the maximum value of the attention map across the pixel coordinates defined by the TRI. The overall perceptual load of the scene is then the sum of the perceptual load contributions of each TRI. TRI coordinates may also be identified using similar extrema or segmentation methods (e.g. local maxima, h-maxima, watershed algorithm, etc.).

As a further example, a "sample and cluster" method may be applied. In this case the attention map is normalised to produce a discrete probability distribution across space, then a number of samples are drawn from this distribution. An unsupervised clustering algorithm can then be applied to identify cluster centers of the samples. Such an algorithm would assume that there exists latent 'objects' that would produce the observed sampling, the location of which we would interpret as the location of the TRIs. This can be achieved with e.g. an iterative Gaussian mixture model (GMM) procedure, which would fit a GMM with one centre, and record the likelihood of the model, then increase the number of centres and observe the likelihood, and compute the Bayesian information criterion (or some other suitable model selection criterion) between the last two models—if that value favours the less complex model (i.e. that with the lower number of centers), then we stop the procedure and select that model. The location of Gaussian centers in that GMM then give the locations of the TRIs from which to calculate the perceptual load across the scene.

As a further example, a "differentiable TRI identification" method may be applied which allows extra supervision. In this case, the TRI identification may be included as a module in the end-to-end driving network itself. This allows the introduction of perceptual load labels to guide the attentional mechanism and produce improved perceptual load estimations. The network's loss function may then include a term which would take into account the perceptual load prediction error as well as the driving command error. The structure of this branch may be a thresholded local-maximum or h-maxima operator (which is differentiable) to identify peaks in the attention distribution and calculate the overall load of the scene according to the general TRI-based approach introduced here. Errors may then backpropagate through the perceptual load estimation module to inform all levels of the whole neural network (and therefore aid in training a more human attentive driving model). Also, classification of TRIs using semantic labels (extracted e.g. from sensors, having been previously mapped) may add weights (for example: child vs adult, bicycle vs motorbike, young vs aged).

Although these are example methods by which to estimate the load of the scene according to cognitive principles, there also exist other simpler methods which approximate our TRI-based methods which also correlate, although less strongly, with perceptual load (as measured by subjective ratings). These include e.g.: the variance across space of the attention map, the maximal value of attention in the attention map, the mean of the attention map, etc.

In addition by using SoA (State-of-Art) semantic labelling techniques such as SegNet (extracted from sensors, and having previously been mapped)

TRIs may be classified, and specific weights may be added as a kind of predictive risk estimation (similar to Japanese concept hiyari hatto, part of the mandatory teachings to driving class students). This may further enable to predict future behaviours of both objects (and the wider context within they exist) and driver desirable control behaviour (e.g. slowing down). For example, within a school zone, and during the day the event of running children and/or flying balls may typically cause higher perceptual load. A narrow street with cars parked on both sides is another example where higher perceptual load is expected.

Another application of estimating perceptual load in driving is to adapt a driving model or agent to the perceptual load of the driving situation. A model may be adapted in real-time to optimal high/low load control patterns, weights, and/or attention maps, when the vehicle enters a high/low load situation, respectively. Similarly, instead of adapting the model, the perceptual load estimate may be used to switch between distinct driving agents specialised to drive in distinct perceptual load conditions.

The attention maps may also be used to guide a vision system's processing allocation (e.g. high-load regions of the scene could undergo finer resolution analysis).

Yet another dimension includes 360° views of said TRIs.

Yet another dimension may be continuous learning whereby the weights of a base model may be updated on the basis of driver's actual driving style. A simpler alternative to this includes factory made pre-sets (low-mid-high) of load sensitivity allowing the driver to customise.

This concept may be combined with an application to assist drivers when they are in a state of 'mind off the road'. For example an attention demanding event can be cued (with a warning signal allowing the driver to maintain safety while in a state of mind off the road).

Furthermore, TRIs may be extracted from any environment and applied to systems supporting humans to safely and/or comfortably interact within (said environment), for example by means of pod type vehicles. Other deployments may include assisted (automated) mobility for impaired persons.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Although the present disclosure herein has been described with reference to particular embodiments, it is to be understood that these embodiments are merely illustrative of the principles and applications of the present disclosure.

It is intended that the specification and examples be considered as exemplary only, with a true scope of the disclosure being indicated by the following claims.

The invention claimed is:

1. A control device for a vehicle for determining perceptual load of a visual and dynamic driving scene,
   the control device being configured to:
   receive an image sequence representing the driving scene,
   extract a set of scene features from the image sequence, the set of scene features representing at least one of static and dynamic information of the driving scene,
   calculate a time-aggregated representation of the image sequence based on the extracted set of scene features,
   calculate an attention map of the driving scene by attentional pooling of the time-aggregated representation of the image sequence, and
   determine the perceptual load of the driving scene based on the attention map.

2. The control device according to claim 1, wherein
   the attention map comprises for each image of the sequence a heat map representing a spatial attention intensity distribution across the image.

3. The control device according to claim 2, wherein the perceptual load of an image is determined based on the heat map of said image.

4. The control device according to claim 1, wherein determining the perceptual load comprises:
   determining at least one spatial and/or temporal peak area of increased attention in the driving scene, and wherein
   the peak area in particular represents a task relevant item.

5. The control device according to claim 2, wherein determining the perceptual load comprises:
   determining at least one spatial and/or temporal peak area of increased attention in the driving scene in combination with determining a contribution value of said peak area to a total value of the perceptual load, and wherein
   the peak area in particular represents a task relevant item.

6. The control device according to claim 4, wherein determining the at least one peak area comprises at least one of threshold-segmenting a heat map to isolate contiguous pixel regions of increased attention, and
   normalizing a heat map to produce a discrete probability distribution, and unsupervised clustering the discrete probability distribution to identify cluster centers of the pixel clusters of increased attention.

7. The control device according to claim 6, wherein determining the at least one peak area comprises at least one of threshold-segmenting each heat map of the driving scene, to isolate contiguous pixel regions of increased attention, and
   normalizing each heat map of the driving scene, to produce a discrete probability distribution, and unsupervised clustering the discrete probability distribution to identify cluster centers of the pixel clusters of increased attention.

8. The control device according to claim 6, wherein unsupervised clustering the discrete probability distribution is made by an iterative Gaussian mixture model.

9. The control device according to claim 5, wherein determining the contribution value of a peak area to the total value of the perceptual load comprises:
   identifying the pixel or neighborhood of pixels which has the highest attention value within the peak area and determining the perceptual load value based on said highest attention value.

10. The control device according to claim 4, wherein determining the perceptual load value of a scene comprises:
    calculating the sum of perceptual load contribution values of the peak areas comprised by the driving scene, in particular including a weighting of the contribution values based on the locations of the peak areas and/or based on a predetermined classification of the peak areas.

11. The control device according to claim 1, wherein the control device comprises a driving model trained to predict driving maneuvers.

12. The control device according to claim 1, wherein the driving model is trained based on training image sequences representing driving scenes.

13. The control device according to claim 12, wherein each of the training image sequences represents a driving scene and is labeled with respective human driving maneuvers carried out during the driving scene.

14. The control device according to claim 1, being further configured to:
    receive information regarding driving maneuvers carried out by the vehicle driver during the driving scene,
    determine based on said information and the determined perceptual load whether the driver is attentive to the driving scene.

15. The control device according to claim 1, wherein the control device comprises at least one of:
    a first neural network for extracting the set of scene features,
    a second neural network for calculating the time-aggregated representation of the image sequence,
    an attentional pooling mechanism for calculating the attention map, and
    an algorithm for determining the perceptual load of the driving scene based on the attention map.

16. The control device according to claim 15, wherein the first neural network is a convolutional neural network and the second neural network is a convolutional long short-term memory network.

17. The control device according to claim 1, wherein the control device comprises a trained load model configured to determine the perceptual load of the driving scene based on the attention map.

18. A method of determining perceptual load of a visual and dynamic driving scene, comprising the steps of:
    a—training a prediction model what includes training a temporal attentional pooling model comprising an attentional pooling mechanism in a supervised manner by using a set of training image sequences, each of said sequences representing a visual and dynamic driving scene and being labeled with respective human driving maneuvers carried out during the driving scene, and
    b—inputting a test image sequence representing an unknown visual and dynamic driving scene into the trained model,
    c—obtaining an attention map from the trained attentional pooling mechanism in response to the inputted test image sequence,
    d—determining the perceptual load of the unknown driving scene based on the attention map.

19. The method according to claim 18, wherein the step of obtaining an attention map further comprises the steps of:
    c1—extracting a set of scene features from the test image sequence, the set of scene features representing at least one of static and dynamic information of the unknown driving scene and of the vehicle,
    c2—calculating a time-aggregated representation of the test image sequence based on the extracted set of scene features, and
    c3—calculating the attention map of the unknown driving scene by attentional pooling of the time-aggregated representation of the test image sequence.

20. The method according to claim 18, wherein the step of training the temporal attentional pooling model further comprises the steps of:
    a1—obtaining a set of training image sequences, each sequence representing a driving scene performed by a human driven vehicle,
    a2—obtaining a data set of human driving maneuvers carried out during the driving scenes,
    a3—training the model in a supervised end-to-end learning manner to learn predicting driving maneuvers by using the set of training image sequences being labeled with the respective human driving maneuvers.

21. The method according to claim 20, wherein the prediction model further comprises a load model, the step of training the prediction model comprising the further steps of:

a4—obtaining a data set of human generated load labels assigned to the human driving maneuvers carried out during the driving scenes, a5—training the load model for predicting the perceptual load of a visual and dynamic driving scene based on the output of the trained attentional pooling mechanism and the human generated load labels, wherein the load model is in particular trained together with the driving model in an end-to-end-manner.

22. The method according to claim 21, wherein human generated load labels are generated by a sensor configured to measure the working memory load at the frontal cortex of the human.

23. The method according to claim 22, wherein the sensor comprises at least one functional near-infrared spectroscopy sensor device.

* * * * *